United States Patent [19]

Griffin et al.

[11] Patent Number: 4,975,112
[45] Date of Patent: Dec. 4, 1990

[54] PYRAZINE COMPOUND USEFUL AS PLANT GROWTH REGULATORS

[75] Inventors: David A. Griffin, Berkshire; Martin J. Rice, Camberley; Raymond Elliott, Berkshire, all of England

[73] Assignee: Imperial Chemical Industries, PLC, London, England

[21] Appl. No.: 209,820

[22] Filed: Jun. 22, 1988

[30] Foreign Application Priority Data

Jun. 22, 1987 [GB] United Kingdom ............... 8714537

[51] Int. Cl.$^5$ .................. A01N 43/60; C07D 241/06
[52] U.S. Cl. ........................................ 71/92; 544/336; 544/406; 544/409
[58] Field of Search ............................ 544/336; 71/92

[56] References Cited

U.S. PATENT DOCUMENTS

| | | | |
|---|---|---|---|
| 3,544,682 | 12/1970 | Taylor et al. | 514/255 |
| 3,928,352 | 12/1975 | Taylor | 544/336 |
| 4,171,214 | 10/1979 | Balasubra-Manyan et al. | 544/336 |
| 4,678,790 | 7/1987 | Dorn et al. | 544/336 |
| 4,902,332 | 2/1990 | Elliott et al. | 71/92 |

FOREIGN PATENT DOCUMENTS 1361816 7/1974 United Kingdom .
2130208 5/1984 United Kingdom .

OTHER PUBLICATIONS

Bus et al., *Recl. Trav. Chim. Pays-Bas*, 92(1): pp. 123–126 (1973).
Kamal et al., *J. Org. Chem.* 27:pp. 1360–1363 (1962).
Behun et al., *J. Am. Chem. Soc.*, 81:5666–5669 (1959).

*Primary Examiner*—Mukund J. Shah
*Assistant Examiner*—E. Bernhardt
*Attorney, Agent, or Firm*—Cushman, Darby & Cushman

[57] ABSTRACT

Pyrazine derivatives useful as plant growth regulating agents have the general formula:

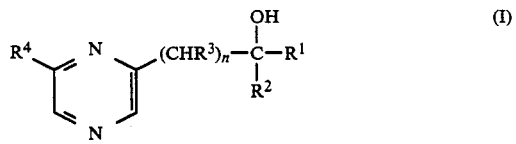

and stereoisomers thereof, wherein $R^1$ is $C_1$–$C_4$ alkyl optionally substituted with halogen, or cyclopropyl optionally substituted with $C_1$–$C_4$ alkyl; $R^2$ is $C_1$–$C_8$ alkyl, $C_2$–$C_8$ alkenyl, or $C_2$–$C_8$ alkynyl each optionally substituted with halogen; $C_3$–$C_6$ cycloalkyl, $C_3$–$C_6$ cycloalkenyl, $C_3$–$C_6$ cycloalkylalkyl, $C_3$–$C_6$ cycloalkenylalkyl, phenylalkenyl or phenylalkynyl each optionally substituted on the ring group; $R^3$ is hydrogen or $C_1$–$C_4$ alkyl; $R^4$ is hydrogen, $C_1$–$C_4$ alkyl, halogen, alkylamino, cyano, or alkoxy; n is 0 or 1; and salts, ethers, acylates and metal complexes thereof.

6 Claims, No Drawings

PYRAZINE COMPOUND USEFUL AS PLANT GROWTH REGULATORS

This invention relates to pyrazine derivatives useful as plant growth regulating agents, to processes for preparing them, to compositions containing them and to methods of regulating plant growth using them.

In British Patent Specification GB No. 1,361,816 and GB No. 1,496,431 there are disclosed certain substituted 2-pyrazine compounds having plant growth regulator activity.

According to the present invention there is provided a pyrazine derivative having the general formula (I) :

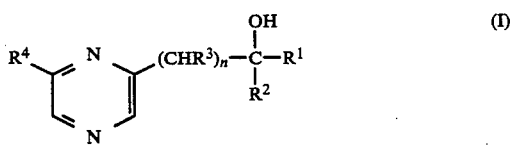

and stereoisomers thereof; wherein $R^1$ is $C_1$–$C_4$ alkyl optionally substituted with halogen, or cyclopropyl optionally substituted with $C_1$–$C_4$ alkyl; $R^2$ is $C_1$–$C_8$ alkyl, $C_2$–$C_8$ alkenyl, or $C_2$–$C_8$ alkynyl optionally substituted with halogen; $C_3$–$C_6$ cycloalkyl, $C_3$–$C_6$ cycloalkenyl, $C_3$–$C_6$ cycloalkenylalkyl, alkenyl, $C_3$–$C_6$ cycloalky phenylalkenyl or phenylalkynyl each optionally substituted on the ring group; $R^3$ is hydrogen or $C_1$–$C_4$ alkyl; $R^4$ is hydrogen, $C_1$–$C_4$ alkyl, halogen, alkylamino, cyano or alkoxy; n is 0 or 1; and salts, ethers, acylates and metal complexes thereof.

The compounds of the invention may contain one or more chiral centres. Such compounds are generally obtained in the form of racemic mixtures. However, these and other mixtures can be separated into the individual isomers by methods known in the art, and this invention embraces such isomers.

When $R^1$ is $C_1$–$C_4$ alkyl, it is preferably tertiary butyl or isopropyl, and when $R^1$ is optionally substituted cyclopropyl, it is preferably 1-methylcyclopropyl.

$R^2$ is preferably straight or branched chain alkyl or alkynyl containing from 3 to 6 carbon atoms, especially alkyl or alkynyl containing 5 to 6 carbon atoms. The $R^2$ group may be optionally substituted with halogen, particularly monohalogen, for example chlorine or fluorine.

When $R^2$ is an alkynyl group, it is preferably a group,

where $R^5$ is an alkyl group containing 3 to 4 carbon atoms and optionally substituted with halogen, preferably chlorine. Especially preferred are the groups n-propyl, isopropyl, n-butyl, isobutyl, sec-butyl and tertiary butyl.

Alternatively when $R^2$ is a phenylalkynyl group, it is preferably a group,

where $R^6$ is a phenyl, optionally substituted with halogen for example chlorine or fluorine.

$R^3$ is preferably hydrogen or methyl when n is 1. Hydrogen is especially preferred. Preferably n is 0. When $R^4$ is halogen, it is preferably chlorine or iodine, when $R^4$ is alkoxy, it is preferably methoxy and when $R^4$ is alkyl-amine, it is preferably dimethylamine. However, the compounds of the invention which are especially preferred are when $R^4$ is hydrogen.

The present invention includes salts, acylates and metal complexes of the compounds of formula (I). As examples of acylates there may be mentioned for example acetates or benzoates. As examples of salts there may be mentioned, for example, toluene sulphonate salts, dodecylbenzene sulphonate salts, hydrochloride salts, hydrobromide salts and orthophosphate salts. Without limitation of the generality of the above statement, the present invention also includes any compound which breaks down in agrochemical use to a compound of formula (I).

Examples of the compounds of the invention are presented in Table I in which the values for $R^1$, $R^2$, $R^3$ and $R^4$ in the general formula (I) above are as indicated.

TABLE I

| COMPOUND NO. | $R_1$ | $R_2$ | $R_3$ | $R_4$ | n | MELTING POINT (°C.) |
|---|---|---|---|---|---|---|
| 1 | t-bu | —C≡C—CH$_2$CH(CH$_3$)$_2$ | — | H | 0 | Oil |
| 2 | i-pr | —C≡C—CH$_2$CH(CH$_3$)$_2$ | — | H | 0 | Oil |
| 3 | t-bu | —C≡C—C$_4$H$_9$ | — | H | 0 | Oil |
| 4 | t-bu | —C≡C—CH(CH$_3$)C$_2$H$_5$ | — | H | 0 | Oil |
| 5 | t-bu | —C≡C—C(CH$_3$)$_3$ | — | H | 0 | 92.0–93.6 |
| 6 | t-bu | —C≡C—C$_3$H$_7$ | — | H | 0 | Oil |
| 7 | i-pr | —C≡C—CH(CH$_3$)C$_2$H$_5$ | — | H | 0 | Oil |
| 8 | i-pr | —C≡C—C(CH$_3$)$_3$ | — | H | 0 | 48.0–50.2 |
| 9 | cyclopropyl | —C≡C—CH$_2$CH(CH$_3$)$_2$ | — | H | 0 | Oil |
| 10 | 1-methylcyclopropyl | —C≡C—CH$_2$CH(CH$_3$)$_2$ | — | H | 0 | Oil |
| 11 | 1-methylcyclopropyl | —C≡C—C$_4$H$_9$ | — | H | 0 | Oil |

TABLE I-continued

| COMPOUND NO. | $R_1$ | $R_2$ | $R_3$ | $R_4$ | n | MELTING POINT (°C.) |
|---|---|---|---|---|---|---|
| 12 | t-bu | —C≡C—C₆H₅ | — | H | 0 | Oil |
| 13 | i-pr | —C≡C—C₆H₅ | — | H | 0 | 76.0–78.0 |
| 14 | cyclopropyl-CH₃ | —C≡C—C₆H₅ | — | H | 0 | 89.0–93.0 |
| 15 | t-bu | —C≡C—C₃H₆Cl | — | H | 0 | 68.8–71.0 |
| 16 | i-pr | —C≡C—C₃H₆Cl | — | H | 0 | Oil |
| 17 | t-bu | —CH₂—C≡C—C₃H₇ | — | H | 0 | Oil |
| 18 | i-pr | —C₃H₆CH(CH₃)₂ | — | H | 0 | Oil |
| 19 | t-bu | —C₅H₁₁ | — | H | 0 | Oil |
| 20 | cyclopropyl-CH₃ | —C₄H₉ | — | H | 0 | Oil |
| 21 | t-bu | —C₆H₁₁ (cyclohexyl) | — | H | 0 | 87.6–89.0 |
| 22 | t-bu | —CH₂—C₆H₁₁ (cyclohexyl) | — | H | 0 | 79.2–80.4 |
| 23 | t-bu | cyclopentyl | — | H | 0 | Oil |
| 24 | t-bu | —CH₂—cyclopentenyl | — | H | 0 | Oil |
| 25 | i-pr | —CH₂—cyclopentenyl | — | H | 0 | 44.8–47.8 |
| 26 | t-bu | —CH₂Cl | — | H | 0 | Oil |
| 27 | t-bu | —C≡C—CH₂CH(CH₃)₂ | H | H | 1 | Oil |
| 28 | t-bu | —C≡C—C(CH₃)₃ | H | H | 1 | 65.6–67.0 |
| 29 | t-bu | —C≡C—C₃H₇ | H | H | 1 | 49.6–51.6 |
| 30 | t-bu | —C≡C—CH(CH₃)₂ | H | H | 1 | Oil |
| 31 | i-pr | —C≡C—C₄H₉ | H | H | 1 | Oil |
| 32 | i-pr | —C≡C—CH₂CH(CH₃)₂ | H | H | 1 | Oil |
| 33 | t-bu | —C≡C—C₃H₇(RR,SS) | CH₃ | H | 1 | 58.4–60.8 |
| 34 | t-bu | —C≡C—C₃H₇(RS,SR) | CH₃ | H | 1 | Oil |
| 35 | t-bu | —C≡C—CH₂CH(CH₃)₂ | — | OCH₃ | 0 | Oil |
| 36 | t-bu | —C≡C—C₆H₅ | — | OCH₃ | 0 | 101.6–103.6 |
| 37 | t-bu | —C≡C—CH₂CH(CH₃)₂ | — | I | 0 | Oil |
| 38 | t-bu | —C≡C—C₆H₅ | — | I | 0 | 74.0–75.6 |

TABLE I-continued

| COMPOUND NO. | $R_1$ | $R_2$ | $R_3$ | $R_4$ | n | MELTING POINT (°C.) |
|---|---|---|---|---|---|---|
| 39 | t-bu | $-C\equiv C-CH_2(CH_3)_2$ | — | $N(CH_3)_2$ | 0 | 75.0–76.4 |
| 40 | t-bu | $-C\equiv C-\text{C}_6H_5$ | — | $N(CH_3)_2$ | 0 | 133.2–136.0 |
| 41 | t-bu | $-C\equiv C-CH_2CH(CH_3)_2$ | — | Cl | 0 | Oil |
| 42 | t-bu | $-C\equiv C-\text{C}_6H_5$ | — | Cl | 0 | 105.8–108.4 |
| 43 | t-bu | $-C\equiv C-\text{C}_6H_5$ | — | CN | 0 | 167.8–169.2 |
| 44 | t-bu | $-C\equiv C-CH_2CH(CH_3)_2$ | — | CN | 0 | 92.4–94.0 |
| 45 | t-bu | $-C_5H_{11}$ | — | $OCH_3$ | 0 | 69.4–72.8 |
| 46 | t-bu | $-C_5H_{11}$ | — | Cl | 0 | Oil |

Compounds of general formula (I) above wherein $R^1$, $R^2$, $R^3$, $R^4$ and n are as defined may be prepared by reacting a compound of general formula (II) or (IIa):

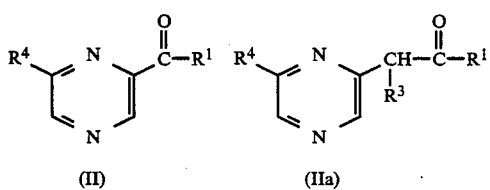

(II)  (IIa)

with an organometallic compound which may be represented by the general formula (III):

$$R^2M \qquad (III)$$

where M is a suitable metal, for example lithium, magnesium, titanium or zirconium.

The reaction conveniently takes place in a solvent such as diethylether, tetrahydrofuran or dichloromethane at −80° C. to +80° C. in an inert atmosphere. The product is obtained by quenching with a proton donor. When M is magnesium, the organometallic compound is more specifically $R^2$-Mg-halogen. When M is titanium, the organometallic compound is more specifically $R^2$-Ti(O-alkyl)$_3$. When M is zirconium, the organometallic compound is more specifically $R^2$-Zr-(O-alkyl)$_3$.

Ketones of the general formula (11) can be prepared from pyrazines and a suitable aldehyde in the presence of an oxidant as outlined in U.S. Pat. No. 4, 588, 813 and EP No. 0076085. Alternatively, the ketones can be prepared by oxidation of the corresponding alcohols (IV), preferably by Jones, Swern or Collins oxidations.

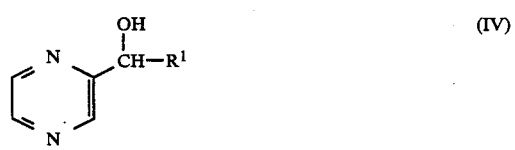

(IV)

The alcohols of general formula (IV) can be prepared by reacting an aldehyde of general formula (V) with an organometallic compound represented by general formula (VI) wherein M is a suitable metal, for example, lithium.

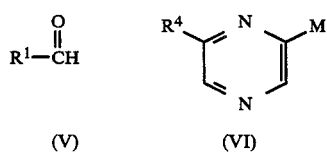

(V)  (VI)

The reaction preferably takes place in a suitable solvent such as diethylether or tetrahydrofuran at a temperature of from −120° C. to +80° C. and in an inert atmosphere. The product is obtained by quenching with a suitable proton donor.

Alternatively, the ketones may be prepared by reacting a compound represented by the general formula (VI) with an ester of general formula (VIa):

(VIa)

The reaction preferably takes place in a suitable solvent such as diethylether or tetrahydrofuran at a temperature from −120° C. to +80° C. and in an inert atmosphere. The product is obtained by quenching with a suitable proton donor.

The compounds of general formula (I) may also be prepared by reacting a ketone of general formula (VII), wherein $R^1$ and $R^2$ are as defined with an organometallic compound which may be represented by the general formula (VI) wherein M is a suitable metal, for example lithium:

(VII)

The reaction preferably takes place in a suitable solvent such as diethylether or tetrahydrofuran at a temperature of from −120° C. to +80° C. and in an inert atmosphere. The product is obtained by quenching with a suitable proton donor.

The ketones of general formula (VII) are known compounds which may be prepared using standard methods set out in the literature.

Ketones of general formula (IIa) may be prepared by reacting a compound of general formula (VIII) with an ester of general formula (VIa) in the presence of a suitable base, for example sodium amide, in a solvent, such as liquid ammonia. The product is obtained by quenching with a suitable proton donor.

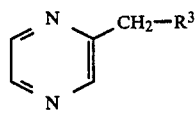

(VIII)

Olefinic alcohols wherein $R^2$ is an alkenyl group may be made by the reduction of the corresponding acetylenic alcohol wherein $R^2$ is $-C{\equiv}C-R^5$. Suitable reducing agents include hydrogen in the presence of a suitable catalyst such as palladium on a support such as carbon; or a metal hydride reducing agent such as lithium aluminium hydride, "Red-Al" (sodium bis [2-methoxyethoxy aluminium] aluminium hydride) or sodium borohydride/palladium (II) dichloride in a suitable solvent such as diethylether or tetrahydrofuran.

Similarly, compounds of formula (I) wherein $R^2$ is an alkyl group may be made by the complete reduction of the corresponding acetylenic alcohol, $-C{\equiv}C-R^5$. Suitable reducing agents include hydrogen in the presence of a suitable catalyst as palladium on a support such as carbon and in a suitable solvent such as methanol, ethanol or acetic acid.

The ethers and acylates of the invention may be made, for example, from the corresponding hydroxy compound by reaction with the appropriate halide, acid chloride or acid anhydride in the presence of a suitable base.

The plant growth regulating effects of the compounds are manifested as, for example, by a stunting or dwarfing effect on the vegetative growth of woody and herbaceous mono- and di- cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased butress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata, Festuca* spp. (e.g., *Festuca rubra*) and *Poa* spp. (e.g., *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (e.g., *Cyperus* spp.) and dicotyledonous weeds (e.g., daisy, plantain, knotweed, speedwell, thistle, docks and ragwort). The growth of non-crop vegetation (e.g., weeds or cover vegetation) can be retarded thus assisting in the maintenance of Plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth o undesirable species.

The dwarfing may also be useful in miniaturising ornamental, household, garden and nursery plants (e.g., poinsettias, chrysanthemums, carnations, tulips and daffodils).

As indicated above, the compounds can also be used to stunt woody species. This property can be used to control hedgerows or to shape or reduce the need for pruning, of fruit trees (e.g., apples, pears, cherries, peaches, vines etc).

The plant growth regulating effect may (as implied above) manifest itself in an increase in crop yield; or in an ability in orchards and other crops to increase fruit set, pod set and grain set. Some coniferous trees are not significantly stunted by the compounds so the compounds could be useful in controlling undesirable vegetation in conifer nurseries.

In the potato, vine control in the field and inhibition of sprouting in the store may be possible.

In addition the compounds may be useful as absicision agents resulting in thinning of fruit on the tree and an increase in fruit quality.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g., wheat, barley, rice, maize, soya, sugarbeet, potatoes, plantation crops and orchard crops The leaf angle effect may be useful for example in altering the leaf orientation of, for example, potato crops thereby letting more light into the crops and inducing an increase in photosynthesis and tuber weight. By increasing tillering in monocotyledonous crops (e.g., rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, e.g., as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, e.g., improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g., turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (i.e. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

It is to be understood that not all the compounds of the present invention will necessarily show all the above mentioned plant growth regulating effects. Thus whilst there may be advantages in compounds which have a broad spectrum of plant growth regulating effects against a wide range of species, compounds having a high specific activity with respect to a particular species and/or plant growth regulating effect may also be of great benefit.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for plant growth regulating purposes but are more conveniently formulated into compositions for such usage. The invention thus provides a plant growth regulating composition comprising a compound of general formula (1) as hereinbefore defined, or a salt or metal complex thereof; and, optionally, a carrier or diluent.

The invention also provides a method of regulating plant growth, which comprises applying to the plant, to seed of a plant or to the locus of a plant or seed, a compound, or a salt or metal complex thereof, as hereinbefore defined, or a composition combining the same.

The compounds, salts, metal complexes, ethers and acylates can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatement. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g., 2-ethoxyethanol and 2-butoxyethanol).

The compositions to be used as sprays may also be in the form of aerosols wherein the formulation is held in a container under pressure in the presence of a propellant, e.g., fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (e.g., nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (1) or a salt or metal complex thereof.

The compositions may also be in the form of liquid preparations for use as dips or sprays which are generally aqueous dispersions or emulsions containing the active ingredient in the presence of one or more surfactants e.g., wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethyl ammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (e.g., alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to for aqueous preparations, m such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also one or more additional compound(s) having biological activity, e.g., compounds having similar or complementary fungicidal or plant growth activity or compounds having plant growth regulating, herbicidal or insecticidal activity.

The additional fungicidal compound can be, for example, one which is capable of combating ear diseases of cereals (e.g., wheat) such as Sepcoria, Gibberella and Helminthosporium spp., seed and soil borne diseases and downy and powdery mildews on grapes and powdery mildew and scab on apple etc. Examples of suitable additional fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenaponil, ofurace, propiconazole, etaconazole and fenpropemorph and fenpropidine.

The compounds of general formula (I) can be mixed with soil, peat or other rooting media for the protection of plants against seed-borne, soil-borne or foliar fungal diseases.

Suitable additional insecticides are Pirimor, Croneton, dimeth- oate, Metasystox, pyrethroid insecticides and formothion.

The other, additional, plant growth regulating compound can be one which controls weeds or seedhead formation, improves the level or longevity of the plant growth regulating activity of the compounds of general formula (I), selectively controls the growth of the less desirable plants (e.g., grasses) or causes the compound of general formula (I) to act faster or slower as a plant growth regulating agent. Some of these other agents will also be herbicides.

Examples of suitable plant growth regulating compounds, which can display synergy in admixture, or use, with the invention compounds are the gibberellins (e.g., $GA_3$, $GA_4$ or $GA_7$), the auxins (e.g., indoleacetic acid, indolebutyric acid, naphthoxyacetic acid or naphthylacetic acid), the cytokinins (e.g., kinetin, diphenylurea, benzimidazole, benzyladenine or benzylaminopurine), phenoxyacetic acids (e.g., 2,4-D or MCPA), substituted benzoic acids (e.g., triiodobenzoic acid), morphactins (e.g., chlorfluorecol), maleic hydrazide, glyphosate, glyphosine, long chain fatty alcohols and acids, dikegulac, fluoridamid, mefluidide, substituted quaternary ammonium and phosphonium compounds (e.g., chlormequat* chlorphonium or mepiquat chloride*), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (e.g., bromoxynil), difenzoquat*, benzoylprop-ethyl 3,6-dichloropicolinic acid, fenpentezol, triapenthanol, flurpirimidol, paclobutrazol, tetcyclacis and tecnazene. Synergy will be most likely to occur with those of the foregoing which are quaternary ammonium compounds and with those marked with an asterisk.

For certain applications, for example in the injection of the compounds of the invention into trees or plants, it is desirable that the compounds have a relatively high solubility in water, for example a solubility in excess of 30 parts per million. The compounds may alternatively be injected into the tree in the form of an organic solution, for example a solution in a lower alcohol.

For certain applications it is also desirable that the compound has a low persistancy in soil to prevent carryover to adjacent crops or even crops planted subsequently in the same soil. Preferably the compound for use in such applications has a half life in the soil of less than 20 weeks.

The invention is illustrated by the following examples, in which Infra red characterisation of the compounds is given as maximum (cm$^{-1}$); NMR characterisation of the compounds is given in terms of H; and mass spectroscopy analysis is given in terms of m/z.

EXAMPLE 1

This Example illustrates the preparation of 2-iodopyrazine.

2-Chloropyrazine (6.18 g, 54 mmol) was added to a saturated solution of sodium iodide in acetone (100 ml) and water (3 ml) at reflux temperature under a nitrogen atmosphere. A solution of hydroiodic acid (3 ml of 55 ) in water (6 ml) was added and the mixture was heated at reflux temperature for 19 hours. The precipitated solids were removed by filtration and the filtrate concentrated under reduced pressure. Water (100 ml) was added to the residue and then solid sodium sulphite until a negative starch iodide test was obtained. Sodium hydroxide pellets were added until the pH was greater than pH 11 and the mixture was continuously extracted with diethylether. The extract was concentrated under reduced pressure and the residue fractionated to give the product as a clear oil (65%, b. pt. 83°-85° C./18 mm Hg).
NMR (90 MHz, CDCl$_3$): 8,88 (1H,m), 8.53 (1H,m), 8.40 (1H, m).
m/z: 206 (M+), 127, 79 (100%).

EXAMPLE 2

This Example illustrates the preparation of 2,6-diiodopyrazine and 2-chloro-6-iodopyrazine.

A solution of dichloropyrazine (60 g, 0.4 mol) in acetone (150 ml) was added to a solution of sodium iodide (500 g, 3.3 mol) in acetone (1800 ml) and water (50 ml) at 60° C. over a period of 10 minutes under a nitrogen atmosphere. Hydroiodic acid (20 ml of 55%) in water (15 ml) was added over a period of 3 hours and heating was continued for a further 30 hours with further identical additions of aqueous acid after 6, 14 and 22 hours. After cooling, solids were removed from the mixture by filtration and the filtrate concentrated under reduced pressure. The residue was taken up in water (1000 ml) and sodium sulphite was added until a negative starch iodide test was obtained. The solution was then made basic to a pH greater than 11 by the addition of sodium hydroxide pellets and then continuously extracted with diethylether over a period of 24 hours. The extract was concentrated and purified by distillation under reduced pressure to give the diiodo compound (25.0 g, 19%) and the chloro-iodo compound (3.0 g, 3%).

2,6-diiodopyrazine

NMR (270 MHz, CDCl$_3$): 8.75 (s).
m/z: 332 (M+), 204, 177, 151, 126 (100%).

2-chloro-6-iodopyrazine m/z: 240 (M+), 126, 115, 113 (100%).

EXAMPLE 3

This Example illustrates the preparation of 3,3-dimethyl-1-(pyrazin-2-yl)-butan-2-one.

Sodium (4.9 g, 0.2 mol) was added slowly to refluxing liquid ammonia (150 g) in the presence of iron (III) nitrate (10 mg). The solution was stirred for 30 minutes after which 2-methylpyrazine (18.8 g, 0.2 mol) was added dropwise over a period of 15 minutes. After a further 30 minutes, ethyl pivaloate (13.0 g, 0.1 mol) in diethylether (20 ml) was added over 20 minutes and the solution stirred for 1 hour. Ammonium chloride (12.5 g) was added to quench the reaction followed by diethylether (100 ml). The ammonia was allowed to evaporate over 15 hours and the residue poured onto ice. Concentrated hydrochloric acid (10 ml) was added and the aqueous layer was extracted with diethylether (2×200 ml). The combined extracts were washed with water and brine, dried over magnesium sulphate and concentrated under reduced pressure. The residue was distilled under reduced pressure and the fraction boiling between 100° C. and 103° C. at 1.1 mm Hg was collected. The product was a yellow liquid (11.1 g, 62%).
Infra red: 1706, 1632, 1476, 1404, 1366, 1326, 1124 cm$^{-1}$.
NMR (90 Mz, CDCl$_3$): 8.40 (3H,m), 3.95 (2H,s), 1.20 (9H, s).
m/z: 178 (M+), 121, 94, 93, 85, 57 (100%).

TABLE II

| Other Compounds Prepared by the method of Example 3 | | |
|---|---|---|
| STARTING MATERIAL | STARTING MATERIAL | PRODUCT |
| pyrazine-CH$_3$ | CH$_3$OCOCH(CH$_3$)CH$_3$ | pyrazine-CH$_2$COCH(CH$_3$)$_2$ |

TABLE II-continued

Other Compounds Prepared by the method of Example 3

| STARTING MATERIAL | STARTING MATERIAL | PRODUCT |
|---|---|---|
| pyrazine-C$_2$H$_5$ | C$_2$H$_5$OCOC(CH$_3$)$_3$ | pyrazine-CH(CH$_3$)COC(CH$_3$)$_3$ |

EXAMPLE 4

This Example illustrates the preparation of 2,2-dimethyl-1-pyraz-2-yl-propan-1-one.

There are three methods which can be used for this preparation.

METHOD A

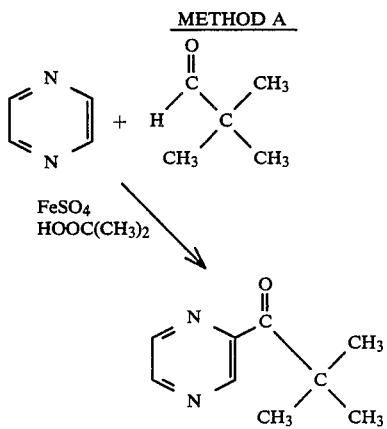

This preparative method can be found in European Pat. No. 0076 085 and U.S. Pat. No. 4,588,813.

METHOD B

STAGE 1: Preparation of 2,2-dimethyl-1-pyrazin-2-yl-propan-1-ol (2-Iodopyrazine was prepared by the method of Example 1).

A solution of 2-iodopyrazine (1.0 g, 4.85 mmol) in dry diethylether (10 ml) was added to a solution of n-butyl lithium (4.04 ml of 1.5M, 6.06 mmol) in dry diethylether (20 ml) at −50° C. over a period of 5 minutes under a nitrogen atmosphere. This was followed immediately by the addition of a solution of pivaldehyde (0.65 g, 7.58 mmol) in dry diethylether (10 ml). The reaction mixture was allowed to warm to room temperature over 4 hours and then poured into a mixture of ice and 10% ammonium chloride solution. The aqueous solution was extracted with diethylether (3×50 ml). The combined extracts were washed with water, dried over magnesium sulphate and concentrated under reduced pressure. The residue was taken up in diethylether and filtered through a bed of silica gel. The filtrate was concentrated under reduced pressure to give the product as a clear oil. (0.76 g, 94%).

Infra red: 3380, 1474, 1402, 1146, 1072, 1018 cm$^{-1}$.
NMR (270 MHz, CDCl$_3$): 8.49 (3H, m), 4.38 (1H, d), 3.61, (1H,d), 0.87 (9H,s).
m/Z: 110 (100%), 109, 57, 41.

STAGE 2: Preparation of 2,2-dimethyl-1-(pyraz-2-yl)-propan-1-one

Concentrated sulphuric acid (2.3 ml) was added dropwise over a period of 5 minutes to a solution of chromium trioxide (2.67 g) dissolved in water (4.0 ml). On completion further water was added to make the volume up to 10 ml. 5 ml of this solution was added dropwise over a period of 1 hour to a solution of 2,2-dimethyl-1-(pyraz-2-yl)-propan-1-ol (2.09 g, 12.6 mmol) in acetone (30 ml) keeping the temperature below 35° C. The mixture was then decanted and the residue washed with acetone (2×5 ml). Excess oxidant was destroyed by addition of isopropanol (1 ml) and the solution was neutralised with sodium hydrogen carbonate. The solution was filtered and concentrated under reduced pressure. Brine (50 ml) was added to the residue and the solution was extracted with diethylether (2×50 ml). The combined extracts were washed with water, dried over magnesium sulphate and concentrated under reduced pressure. The product was obtained as a clear oil (1.14 g, 55%).

Infra red: 1686, 1568, 1480, 1460, 1394, 1364, 1292, 1216 cm$^1$.
NMR (90 MHz, CDCl$_3$): 9.08 (1H, m), 8.64 (1H, m), 8.58, (1H, m), 1.42 (9H, s).
m/z: 164 (M$^+$), 136, 109, 108, 94, 81, 80, 79, 57 (100%).

METHOD C

To a solution of 2-iodopyrazine (5.0 g, 24 mmol) and ethylpivaloate (2.5 g, 19 mmol) in dry diethylether (100 ml), a solution of n-butyl lithium (9.84 ml of 2.5M, 24 mmol) in hexanes was added at −70° C. over a period of 20 minutes under a nitrogen atmosphere. The reaction mixture was stirred for 1 hour at −70° C. after which saturated ammonium chloride solution (2 ml) was added. The solution was allowed to warm to room temperature over 4 hours and was poured into saturated ammonium chloride solution (200 ml). The aqueous layer was extracted with diethylether (2×100 ml) and the combined extracts washed with saturated ammonium chloride solution, brine, dried over magnesium sulphate and concentrated under reduced pressure. The residue was taken up in diethylether, filtered and concentrated under reduced pressure. The residue was purified by preparative HPLC on silica gel, eluting with diethylether/hexane (3:1) giving the product as a clear oil (1.3 g, 41%).

TABLE III

Other Compounds Prepared by the method of Example 4

| STARTING MATERIAL | STARTING MATERIAL | PRODUCT |
|---|---|---|
| 2-iodopyrazine | $C_2H_5OCOCH(CH_3)_2$ | 2-(isobutyrl)pyrazine |
| 2,6-diiodopyrazine | $C_2H_5OCOC(CH_3)_3$ | 2-iodo-6-(pivaloyl)pyrazine |
| 2-methoxy-6-iodopyrazine | $C_2H_5OCOC(CH_3)$ | 2-methoxy-6-(pivaloyl)pyrazine |
| 2-iodopyrazine | $C_2H_5OCO$-cyclopropyl | 2-(cyclopropylcarbonyl)pyrazine |
| 2-iodopyrazine | $C_2H_5OCO$-(1-methylcyclopropyl) | 2-(1-methylcyclopropylcarbonyl)pyrazine |
| 2-iodopyrazine | $C_2H_5OCO$-(1-methylcyclopropyl) | Compound 20 of Table I* |

*Compound 20 of Table I was prepared during preparation of 2-(1-methylcyclopropylcarbonyl)pyrazine.

NMR (CDCl$_3$) 270 MHz: 8.76 (1H, m), 8.51 (2H, m), 4.38 (1H, s), 1.90 (2H, m), 1.22 (3H, m), 0.84 (8H, m), 0.30 (1H, m), 0.10 (2H, m).
m/s: 200 (M+), 165, 164, 163, 108, 94 (100%).

EXAMPLE 5

This Example illustrates the preparation of 2,7-dimethyl-3-(pyraz-2-yl)-octan-3-ol, Compound No. 18 of Table 1.

(2-Iodopyrazine was prepared by the method of Example 1).

N-butyl lithium (6.1 ml of 1.6M, 9.7mmol) was added to a solution of 2-iodopyrazine (2.9 g, 9.7mmol) and 2,7-dimethyloctan-3-one (1.20 g, 7.7mmol) in dry diethylether (50 ml) at −78° C. over a period of 20 minutes under a nitrogen atmosphere. The mixture was stirred for a further 90 minutes at −78° C. Saturated ammonium chloride solution (2 ml) was added and the mixture allowed to warm to room temperature over 4 hours. The mixture was poured in to saturated ammonium chloride solution and extracted with diethylether (2×50 ml). The combined extracts were washed with saturated ammonium chloride solution, dried over magnesium sulphate and concentrated under reduced pressure. The residue was purified by preparative HPLC on silica gel, eluting with diethylether/hexane (3:1), the product being obtained as a yellow oil [0.50 g, 28%].
Infra red: 34560, 1460, 1385, 1170, 1130 cm$^{-1}$.

TABLE IV

Other Compounds Prepared by this Method

| COMPOUND NO. OF TABLE I | STARTING MATERIAL | STARTING MATERIAL | NMR DATA |
|---|---|---|---|
| 19 | 2-iodopyrazine | $(CH_3)_3CCOC_5H_{11}$ | 8.50 (3H, m), 4.65 (1H, s), 2.00 (2H, m), 1.22 (6H, m), 0.91 (9H, s), 0.80 (3H, m). |
| 21 | 2-iodopyrazine | $(CH_3)_3CCO$-cyclohexyl | 8.80 (1H, m), 8.48 (2H, m), 4.80 (1H, s), 2.18 (2H, m), 1.80 (1H, m), 1.58 (2H, m), 1.20 (4H, m), 0.94 (9H, s), 0.84 (2H, m). |

TABLE IV-continued

Other Compounds Prepared by this Method

| COMPOUND NO. OF TABLE I | STARTING MATERIAL | STARTING MATERIAL | NMR DATA |
|---|---|---|---|
| 22 | pyrazine-I | $(CH_3)_3CCOCH_2$—cyclohexyl | 8.72 (1H, s), 8.49 (2H, m), 4.65 (1H, s), 1.96 (2H, m), 1.88 (1H, m), 1.49 (4H, m), 1.10 (5H, m), 0.88 (9H, s), 0.70 (1H, m). |
| 23 | pyrazine-I | $(CH_3)_3CCO$—cyclopentenyl | 8.81 (1H, s), 8.51 (2H, m), 5.00 (1H, s), 2.80 (1H, m), 1.60 (6H, m), 0.98 (9H, s), 0.96 (2H, m). |
| 24 | pyrazine-I | $(CH_3)_3CCOCH_2$—cyclopentenyl | 8.76 (1H, m), 8.50 (2H, m), 6.60 (2H, m), 4.80 (1H, m), 2.19 (5H, m), 1.60 (1H, m), 1.13 (1H, m), 0.91 (9H, m). |
| 25 | pyrazine-I | $(CH_3)_2CHCOCH_2$—cyclopentenyl | 8.75 (1H, m), 8.52 (2H, m), 5.62 (3H, m), 4.98 (1H, m), 4.39 (1H, s), 2.06 (8H, m), 1.03 (3H, m), 0.64 (3H, m). |
| 45 | $CH_3O$-pyrimidine-I | $(CH_3)_3CCOC_5H_{11}$ | 8.20 (1H, s), 8.12 (1H, s), 4.20 (1H, s), 3.99 (3H, s), 2.00 (2H, m), 1.24 (6H, m), 0.91 (9H, s), 0.82 (3H, m). |
| 46 | Cl-pyrimidine-I | $(CH_3)_3CCOC_5H_{11}$ | 8.59 (1H, s), 8.48 (1H, s), 3.83 (1H, s), 2.12 (1H, m), 1.92 (1H, m), 1.22 (4H, m), 0.90 (9H, s), 0.81 (4H, m), 0.60 (1H, m). |

NMR (400 MHz, CDCl$_3$): 8.60 (3H, m), 4.31 (1H, s), 2.08, (1H, m), 1.97 (1H, m), 1.82, (1H, m), 1.42 (1H, m), 1.28 (1H, m), 1.10, (2H, m), 1.00 (3H, m), 0.78, (6H, m), 0.65 (5H, m).
m/z: 237 (M$^+$) (100%).

EXAMPLE 6

This Example illustrates the preparation of 2,2-dimethyl-1-(hex-2-yne)-1-(pyraz-2-yl)-propan-1-ol, Compound No. 17 of Table 1 and 2,2-dimethyl-1-(chloromethane)-1-(pyraz-2-yl)-propanol, Compound No. 26 of Table I.

STAGE 1: Preparation of 3,3-dimethyl-2-(pyraz-2-yl)-but-1-ene oxide (2,2-Dimethyl-1-(pyraz-2-yl)-propan-1-one is prepared by the method of Example 4).

powdered potassium hydroxide (218 mg) was added to a solution of 2,2-dimethyl-1-(pyraz-2-yl)-propan-1-one (300 mg, 1.82 mmol) and trimethylsulphonium iodide (382 mg, 1.87 mmol) in dimethyl sulphoxide (4 ml). The resulting mixture was stirred for 2 hours under a nitrogen atmosphere and then partitioned between diethylether and water. The aqueous layer was extracted with ether and the combined organic extracts were washed with dilute hydrochloric acid, saturated solution of sodium hydrogen carbonate and water. After drying over magnesium sulphate, the solution was concentrated under reduced pressure to give the product as a clear oil (260 mg, 80%).

Infra red: 1478, 1400, 1366, 1150, 1080, 1042 cm$^{-1}$.
NMR (270 MHz, CDCl$_3$): 9.70 (1H, s), 9.50 (2H, m), 3.15, (1H, d), 2.69 (1H,d) 1.05 (9H,s).
m/z: 178(M$^+$), 163, 147, 133, 122, 107, 94 (100%).

STAGE 2:

A solution of ethyl magnesium chloride (1.02 ml of 2M, 2.40 mmol) in diethylether was added to a solution of pent-1-yne (139 mg, 2.04 mmol) in dry tetrahydrofuran [20 ml] at 20° C. under a nitrogen atmosphere. The mixture was stirred for 3 hours. 3,3-dimethyl-2-(Pyraz-2-yl)-but-1-ene oxide (290 mg, 163 mmol) in tetrahydrofuran (10 ml) was added to the reaction mixture over a period of 5 minutes and the resulting solution was heated at reflux temperature for 3 hours. After cooling, the mixture was partitioned between ethyl acetate and water. The aqueous layer was extracted with ethyl acetate and the combined organic layers were washed with water, dried over magnesium sulphate and concentrated under reduced pressure. The residue was purified by preparative HPLC on silica gel, eluting with diethylether/hexane (1:1), giving Compound No. 17 as a clear oil (60 mg, 25%) and Compound No. 26 as a clear oil (70 mg, 34%).

Compound No. 17:

NMR (270 MHz, CDCl$_3$): 8.87 (1H,s), 8.54 (1H, d), 8.46, (1H, d), 3.96 (1H, s), 3.25 (1H, m), 2.82 (1H, m), 1.95, (2H, m), 1.25 (2H, m), 0.94 (9H, s), 0.68 (3H, t).
m/z: 246 (M$^+$), 218, 189, 165 (100%), 161, 147.

Compound No. 26:
NMR (270 MHz, CDCl₃): 8.86 (1H, s), 8.52 (2H, m), 4.57 (1H, d), 4.06 (1H, d), 3.92 (1H, s), 0.98 (9H, s).
m/z: 199, 178, 158, 147, 123 (100%).

EXAMPLE 7

This Example illustrates the preparation of 2,2-dimethyl-1-(4-methylpent-1-yne)-1-(pyraz-2-yl)-propan-1-ol, Compound No. 1 of Table I.

(2,2-Dimethyl-1-(pyraz-2-yl)-propan-1-one is prepared by the method of Example 4).

A solution of n-butyl lithium (2.5 ml of 1.5M, 3.75 mmol) was added to a solution of 4-methylpent-1-yne (0.30 g, 3.66 mmol) in dry tetrahydrofuran (5 ml) at 0° C. over a period of 5 minutes under a nitrogen atmosphere. The mixture was stirred at 0° C. for 20 minutes after which it was cooled to −55° C. A solution of 2,2-dimethyl-1-(pyraz-2-yl)-propan-1-one in dry tetrahydrofuran (5 ml) was added to the reaction mixture over a period of 5 minutes. The mixture was allowed to warm to room temperature over 3 hours and methanol (1 ml) was added. The solution was poured into water (30 ml) and extracted with diethylether. The combined extracts were washed with water, dried over ma9nesium sulphate and concentrated under reduced pressure, the product being obtained as a clear oil (0.63 g, 84%).

Infra red: 3430, 2238, 1462, 1396, 1266, 738 cm⁻¹.
NMR (270 MHz, CDCl₃): 8.92 (1H, m), 8.46 (1H, m), 8.42, (1H, m), 4.84 (1H, s), 2.12 (2H, d), 1.80 (1H, m), 0.96 (15H, m).
m/z: 246 (M+), 231, 190 (100%), 165.

TABLE V

Other Compounds Prepared by the method of Example 7

| COMPOUND NO. OF TABLE I | STARTING MATERIAL | STARTING MATERIAL | NMR DATA |
|---|---|---|---|
| 3 | 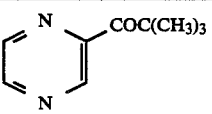 | HC≡C—C₄H₉ | 9.00(1H, m), 8.54(2H, m), 4.90 (1H, s), 2.32(2H, t), 1.50(4H, m), 1.00(9H, s), 0.93(3H, t). |
| 4 | 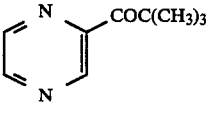 | HC≡C—CH(CH₃)C₂H₅ | 9.00(1H, m), 8.54(2H, m), 4.92 (1H, s), 2.48(1H, m), 1.52(2H, m), 1.20(3H, m), 1.02(3H, m), 1.00(9H, s). |
| 5 | 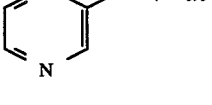 | H—C≡C—C(CH₃)₃ | 8.98(1H, m), 8.46(2H, m), 4.84 (1H, s), 1.36(9H, s), 1.00(9H, s). |
| 6 | 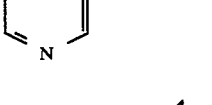 | H—C≡C—C₃H₇ | 9.00(1H, m), 8.50(2H, m), 4.82 (1H, s), 2.26(2H, t), 1.60(2H, m) 1.02(3H, t), 1.00(9H, s). |
| 10 | 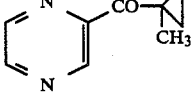 | H—C≡C—CH₂CH(CH₃)₂ | 8.96(1H, m), 8.45(2H, m), 4.92 (1H, s), 2.08(2H, d), 1.80(1H, m), 0.90(13H, m). |
| 11 | 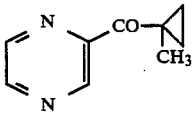 | H—C≡C—C₄H₉ | 8.98(1H, m), 8.50(2H, m), 4.84 (1H, s), 2.20(2H, m), 1.20(14H, m). |
| 12 | 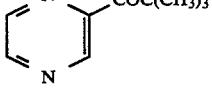 | H—C≡C—C₆H₅ | 9.08(1H, m), 8.57(2H, m), 7.40 (5H, m), 5.00(1H, s), 1.08(9H, s). |
| 14 | 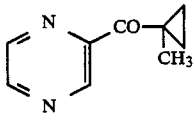 | H—C≡C—C₆H₅ | 9.04(1H, m), 8.58(2H, m), 7.36 (5H, m), 5.04(1H, s), 1.22(2H m), 0.96(3H, s), 0.50(2H, m). |
| 15 | 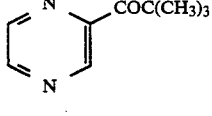 | H—C≡C—C₃H₆Cl | 8.98(1H, m), 8.53(2H, m), 4.94 (1H, s), 3.68(2H, t), 2.52(2H, t), 2.02(2H, m), 1.00(9H, s). |

TABLE V-continued
Other Compounds Prepared by the method of Example 7

| COMPOUND NO. OF TABLE I | STARTING MATERIAL | STARTING MATERIAL | NMR DATA |
|---|---|---|---|
| 34 | pyrazine-CH(CH$_3$)COC(CH$_3$)$_3$ (RS,SR) | H—C≡C—C$_3$H$_7$ | 8.46(3H, m), 4.98(1H, s), 3.38 (1H, q), 2.25(2H, t), 1.58(5H, m), 1.01(3H, t), 0.88(9H, s). |
| 35 | CH$_3$O-pyrazine-COC(CH$_3$)$_3$ | H—C≡C—CH$_2$CH(CH$_3$)$_2$ | 8.50(1H, s), 8.18(1H, s), 4.58 (1H, s), 4.00(3H, s), 2.20(2H, d), 1.90(1H, m), 1.02(6H, d), 1.00(9H, s). |
| 36 | CH$_3$O-pyrazine-COC(CH$_3$)$_3$ | H—C≡C—C$_6$H$_5$ | 8.60(1H, s), 8.22(1H, s), 7.40 (5H, m), 4.64(1H, s), 4.00(3H, s), 1.08(9H, s). |
| 37 | I-pyrazine-COC(CH$_3$)$_3$ | H—C≡CCH$_2$CH(CH$_3$)$_2$ | 8.88(1H, s), 8.78(1H, s), 4.43 (1H, s), 2.19(2H, d), 1.86(1H, m), 1.03(6H, d), 1.01(9H, s). |
| 38 | I-pyrazine-COC(CH$_3$)$_3$ | H—C≡C—C$_6$H$_5$ | 8.89(1H, s), 8.74(1H, s), 7.40 (2H, m), 7.28(3H, m), 4.53(1H, s), 1.01(9H, s). |
| 39 | (CH$_3$)$_2$N-pyrazine-COC(CH$_3$)$_3$ | H—C≡C—CH$_2$CH(CH$_3$)$_2$ | 8.18(1H, s), 7.94(1H, s), 5.24 (1H, s), 3.13(6H, s), 2.20(2H, d), 1.88(1H, m), 1.04(6H, d), 1.02(9H, s). |
| 40 | (CH$_3$)$_2$N-pyrazine-COC(CH$_3$)$_3$ | H—C≡C—C$_6$H$_5$ | 8.18(1H, s), 7.90(1H, s), 7.42 (2H, m), 7.24(3H, m), 5.34(1H, s), 3.08(6H, s), 1.02(9H, s). |
| 41 | Cl-pyrazine-COC(CH$_3$)$_3$ | H—C≡C—CH$_2$CH(CH$_3$)$_2$ | 8.88(1H, s), 8.53(1H, s), 4.31 (1H, s), 2.20(2H, d), 1.88(1H, m), 1.02(15H, m). |
| 42 | Cl-pyrazine-COC(CH$_3$)$_3$ | H—C≡C—C$_6$H$_5$ | 8.98(1H, s), 8.58(1H, s), 7.40 (5H, m), 4.40(1H, s), 1.08(9H, s). |

EXAMPLE 8

This Example illustrates the preparation of 2-methyl-1-(4-methyl pent-1-yne)-1-(pyraz-2-yl)-propan-1-ol, Compound No. 2 of Table I.

(2-Methyl-1-(pyraz-2-yl)-propan-1-one is prepared by the method of Example 4).

A solution of n-butyl lithium (5.92 ml of 1.5M, 8.88 mmol) was added to a solution of 4-methylpent-1-yne (0.68 g, 8.88 mmol) in dry tetrahydrofuran (20 ml) at 0° C. over a period of 5 minutes under a nitrogen atmosphere. The mixture was stirred at 0° C. for 30 minutes after which it was cooled to −35° C. Chlorotitanium triisopropoxide (8.88 ml of 1.0M in hexanes, 8.88 mmol) was added over a period of 5 minutes and stirring was continued for a further 20 minutes at −35° C. A solution of 2-methyl-1-pyraz-2-yl-propan-1-one (1.0 g, 6.67 mmol) in dry tetrahydrofuran (10 ml) was added over a period of 10 minutes and the mixture allowed to warm to room temperature over 20 hours. Ammonium chloride solution (10 ml of 20%) added and the precipitated material removed by filtration and washed with ethyl acetate and water. The combined filtrate and washings were extracted with ethyl acetate (3×50 ml) and the combined extracts washed with water and brine, dried over magnesium sulphate and concentrated under reduced pressure. The residue was purified by preparative HPLC on silica gel, eluting with diethylether/hexane (1:1), to give the product as a clear oil (0.31 g, 20%). Infra red: 3410, 1464, 1402, 1164, 1014, 840 cm$^{-1}$.

NMR (90 MHz, CDCl$_3$): 8.96 (1H, m), 8.49 (2H, m), 4.25, (1H, s), 2.20 (2H, d), 2.10 (2H, m), 100 (12H, m).
m/z: 232(M$^+$), 217, 89, 79 (100%).

EXAMPLE 9A

This Example illustrates the preparation of RS,SR 4,4-dimethyl-3-(pent-1-yne)-2-(pyraz-2-yl)-pentan-3-ol, Compound No. 34 of Table 1.

TABLE VI
Other Compounds Prepared by the method of Example 8

| COMPOUND NO. OF TABLE I | STARTING MATERIAL | STARTING MATERIAL | NMR DATA |
|---|---|---|---|
| 7 | pyrazinyl-COCH(CH$_3$)$_2$ | H—C≡C—CH(CH$_3$)C$_2$H$_5$ | 8.97(1H, s), 8.53(2H, m), 4.32(1H, s), 2.52(1H, m), 2.18(1H, m), 1.52(2H, m), 1.21(3H, d), 0.99(9H, m). |
| 8 | pyrazinyl-COCH(CH$_3$)$_2$ | H—C≡C—C(CH$_3$)$_3$ | 8.96(1H, s), 8.53(2H, m), 4.26(1H, s), 2.12(1H, m), 1.28(9H, s), 0.95(6H, d). |
| 9 | pyrazinyl-CO-cyclopropyl | H—C≡C—CH$_2$CH(CH$_3$)$_2$ | 9.00(1H, m), 8.53(2H, m), 4.62(1H, s), 2.12(2H, m), 1.80(1H, s), 1.28(1H, m), 0.98(6H, m), 0.80(2H, m), 0.58(2H, m). |
| 13 | pyrazinyl-COCH(CH$_3$)$_2$ | H—C≡C—phenyl | 9.04(1H, s), 8.56(2H, m), 7.40(5H, m), 4.54(1H, s), 2.29(1H, m), 1.10(3H, d), 0.97(3H, d). |
| 16 | pyrazinyl-COCH(CH$_3$)$_2$ | H—C≡C—C$_3$H$_6$Cl | 9.94(1H, s), 8.52(2H, m), 4.40(1H, s), 3.67(2H, t), 2.51(2H, t), 2.18(1H, m), 2.02(2H, m), 1.00(3H, d), 0.88(3H, d). |
| 27 | pyrazinyl-CH$_2$COC(CH$_3$)$_3$ | H—C≡C—CH$_2$CH(CH$_3$)$_2$ | 8.49(3H, m), 5.11(1H, s), 3.07(2H, m), 1.87(2H, d), 1.58(1H, m), 1.16(9H, s), 0.77(6H, m). |
| 28 | pyrazinyl-CH$_2$COC(CH$_3$)$_3$ | H—C≡C—C(CH$_3$)$_3$ | 8.52(3H, m), 4.78(1H, s), 3.05(2H, m), 1.16(9H, s), 0.98(9H, s). |
| 29 | pyrazinyl-CH$_2$COC(CH$_3$)$_3$ | H—C≡C—C$_3$H$_7$ | 8.48(3H, m), 5.00(1H, s), 3.06(2H, m), 1.98(2H, t), 1.30(2H, m), 1.15(9H, s), 0.75(3H, t). |
| 30 | pyrazinyl-CH$_2$COC(CH$_3$)$_3$ | H—C≡C—CH(CH$_3$)$_2$ | 8.55(3H, m), 4.87(1H, s), 3.06(2H, m), 2.35(1H, m), 1.14(9H, s), 0.88(6H, m). |
| 31 | pyrazinyl-CH$_2$COCH(CH$_3$)$_2$ | H—C≡C—C$_4$H$_9$ | 8.56(3H, m), 5.04(1H, s), 3.10(2H, m), 2.04(2H, m), 1.94(1H, m), 1.30(4H, m), 1.11(6H, m), 0.81(3H, t). |
| 32 | pyrazinyl-CH$_2$COCH(CH$_3$)$_2$ | H—C≡C—CH$_2$CH(CH$_3$)$_2$ | 8.49(3H, m), 5.14(1H, s), 3.11(2H, m), 1.93(2H, d), 1.96(1H, m), 1.62(1H, m), 1.12(6H m), 0.80(6H, m). |

In the preparation of Compound No. 34 of Table 1 4,4-dimethyl-2-(pyraz-2-yl)-pentan-3-one was prepared by the method of Example 3 and used in the method of Example 7 to obtain the end product.

EXAMPLE 9B

This Example illustrates the preparation of RR,SS 4,4-dimethyl-3-(pent-1-yne)-2-(pyraz-2-yl)-pentan-3-ol, Compound No. 33 of Table 1.

(4,4-Dimethyl-2-(pyraz-2-yl)-pentan-3-one was prepared by the method of Example 3).

A solution of ethyl magnesium bromide in diethylether (3.5 ml of 3M, 10 mmol) was added to a solution of pent-1-yne (0.71 g, 10 mmol) and dry tetrahydrofuran (30 ml) at 0° C. over a period of 20 minutes under a nitrogen atmosphere. The mixture was stirred for 10 minutes and heated at reflux temperature for a further 1 hour after which the mixture was cooled to 0° C. A solution of 4,4-dimethyl-2-(pyraz-2-yl)-pentan-3-one (1.0 g, 5.2 mmol) in dry tetrahydrofuran (20 ml) was added to the reaction mixture over 20 minutes and stirring was continued at 0° C. for 1 hour. The mixture as poured into water and was extracted with ethyl acetate (3×50 ml). The combined extracts were washed with Water and brine, dried over magnesium sulphate and concentrated under reduced pressure. The residue was purified by preparative HPLC on silica gel, eluting with diethylether and the major fraction was triturated with hexane to give the product as a yellow solid (0.27 g, 20%, m.pt 58.4°-60.8° C.). Gas chromatography showed that the product contained 3% of the RS,SR diastereoisomer.

Infra red: 3190, 2250, 1465, 1400, 1150, 990 cm$^{-1}$.

NMR: 8.59 (1H, m), 8.43 (2H, m) 4.20 (1H, s), 3.40 (1H, q), 1.96 (2H, t), 1 43 (3H, d), 1.29 (2H, m), 1.08 (9H, s), 0.79 (3H, t).

m/z: 203, 189, 175, 153, 135, 108 (100%), 107.

EXAMPLE 10

This Example illustrates the preparation of 2,2-dimethyl-1-(4-methylpent-1-yne)-1-(pyraz-2-ylmethyl)-propan-1-ol, Compound No. 27 of Table I.

2,2-Dimethyl-1-(pyraz-2-ylmethyl)-propan-1-one was prepared by the method of Example 3 and used in the method of Example 8 to obtain the final product. Compound Nos. 28, 29, 30, 31 and 32 of Table I were also prepared by this route.

EXAMPLE 11

This Example illustrates the preparation of 2,2-dimethyl-1-(4-methylpent-1-yne)1-(6-chloropyraz-2-yl)-propan-1-ol, Compound No. 41 of Table I.

2-Chloro-6-iodopyrazine was prepared by the method of Example 2 and used in the method of Example 4 for the preparation of 2,2-dimethyl-1-(3-choropyraz-2-yl)-propan-1-one. The product of Example 4 was used in the method of Example 7 to obtain the end product. Compound No. 42 of Table I was also prepared by this route.

EXAMPLE 12

This Example illustrates the preparation of 2,2-dimethyl-3-(6-chloropyraz-2-yl)-octan-3-ol, Compound No. 46 of Table I.

2-Chloro-6-iodopyrazine was prepared by the method of Example 2 and used in the method of Example 5 for the preparation of the end product.

EXAMPLE 13

This Example illustrates the preparation of 2,2-dimethyl-1-(4-methylpent-1-yne)-1-(N,N-dimethyl-6-amino-pyraz-2-yl)-propan-1-ol, Compound No. 39 of Table I.

STAGE 1: 2,6-Iodopyrazine was prepared by the method of Example 2 and used in the method of Example 4 for the preparation of 2,2-dimethyl-1-(6-iodopyraz-2-yl)propan-1-one.

STAGE 2: Preparation of 2,2-dimethyl-1-(N,N-dimethyl-6-amino-pyraz-2-yl)propan-1-one 2,2-Dimethyl-1-(6-iodopyraz-2-yl)propan-1-one (0.5 g, 1.72 mmol) was added to an aqueous solution of dimethylamine (5 ml of 40% w/w) and the mixture heated at reflux temperature for 90 minutes. After cooling, the mixture was poured into water and extracted twice with diethylether. The combined organic layers were washed with water, dried over magnesium sulphate and concentrated under reduced pressure to give the product as a yellow solid (360 mg, 100%) m. pt. 60.4°-61.6° C.

Infra red: 1680, 1580, 1460, 1380, 1210 cm$^{-1}$.

NMR (270 MHz, CDCl$_3$): 8.21 (1H, s), 8.02 (1H, s), 3.08 (6H, s), 1.32 (9H, s).

m/z: 207(M+), 137, 123, 121(100%), 95, 57.

STAGE 3: The product of Stage 2 above was used in the method of Example 7 to obtain Compound No. 39 of Table I. Compound No. 40 of Table I was also prepared by this route.

EXAMPLE 14

This Example illustrates the preparation of 2,2-dimethyl-1-(6-cyanopyraz-2-yl)-1-(2-phenylethyne)-propan-1-ol, Compound No. 43 of Table I via 2,2-dimethyl-(6-iodopyraz-2-yl)-1-(2-phenylethyne)-propan-1-ol, Compound No. 38 of Table I.

2,2-Dimethyl-1-(6-iodopyraz-2-yl)-1-(2-phenylethyne)-propan-1-ol was prepared by the method of Example 7 from 2,2-dimethyl-1-(6-iodopyraz-2-yl)-propan-1-one. 2,2-dimethyl-1-(6-iodopyraz-2-yl)-propan-1-one was prepared by the method of Example 4 from 2,6-diiodopyrazine. 2,6-diiodopyrazine was prepared by the method of Example 2 from the starting material 2,6-dichloropyrazine.

Copper (I) cyanide (0.17 g, 19 mmol) was added to a solution of 2,2-dimethyl-1-(6-iodopyraz-2-yl)-1-(2-phenylethyne)-propan-1-ol (0.5 g, 1.3 mmol) in dimethylformamide (20 ml) and the mixture heated at reflux temperature for 6 hours under a nitrogen atmosphere. After cooling, the reaction mixture was poured into a solution of ferric chloride in 2N hydrochloric acid. The acidic solution was extracted twice with dichloromethane and the combined organic layers were washed with water until the washings were neutral, dried over magnesium sulphate and concentrated under reduced pressure. The residue was purified by preparative HPLC on silica gel, eluting with dichloromethane, giving the product as a white solid (0.11 g, 30%) m. pt. 167.8°-169.2° C.

NMR (270 MHz, CDCl$_3$): 9.28 (1H, s), 8.90 (1H, s), 7.40 (5H, m), 4.24 (1H, s), 1.10 (9H, s).

m/z: 235, 131, 105, 104, 77, 57(100%).

Compound No. 44 was also prepared by this route via Compound No. 37 (Table VII).

TABLE VII

| COMPOUND NO. OF TABLE I | STARTING MATERIAL | NMR DATA |
| --- | --- | --- |
| 44 | I—[pyrazine]—C(OH)[(C(CH$_3$)$_3$)(C≡CCH$_2$CH(CH$_3$)$_2$)] | 9.19 (1H, s), 8.84 (1H, s), 4.11 (1H, s), 2.20 (2H, m), 1.91 (1H, m), 1.02 (15H, m). |

EXAMPLE 15

This Example illustrates the preparation of 2,2-dimethyl-1-(4-methylpent-1-yne)-1-(6-methoxypyraz-2-yl)-1-propan-1-ol, Compound No. 35 of Table I.

STAGE 1:

2,6-Diiodopyrazine is prepared from 2,6-dichloropyrazine by the method of Example 2.

STAGE 2: preparation of 2-iodo-6-methoxypyrazine 2,6-Diiodopyrazine (5.0 g, 15 mmol) was added to a solution of sodium methoxide in methanol (prepared from sodium (0.35 g, 15 mmol) and methanol (40 ml)) and the mixture was heated at reflux temperature for 1 hour. After cooling, the solution was diluted with water (200 ml) and extracted with diethylether (3×100 ml). The combined extracts were washed with water, dried over magnesium sulphate and concentrated under reduced pressure to give the product as a white solid (3.5 g, 100%) m. pt. 35.7–37.2

NMR (90 MHz, CDCl$_3$): b 8.40 (1H, s), 8.16 (1H,s), 3.98 (3H,s).

m/z 236(M+), 127, 109 (100%).

STAGE 3:

2,2-Dimethyl-1-(6-methoxypyraz-2-yl)-propan-1-one was prepared from 2-iodo-6-methoxypyrazine by the method of Example 4.

STAGE 4: 2,2-dimethyl-1-(4-methylpent-1-yne)-1-(6-methoxy-pyraz-2-yl)-1-propan-1-ol was prepared from 2,2-dimethyl-1-(6-methoxypyraz-2-yl)-propan-1-one by the method of Example 7. Compound No. 36 of Table I was also prepared by this route.

EXAMPLE 16

This Example illustrates the preparation of 2,2-dimethyl-3-(6-methoxypyraz-2-yl)-octan-3-ol, Compound No. 45 of Table I.

STAGE 1: 2,6-Diiodopyrazine is prepared from 2,6-dichloro-pyrazine by the method of Example 2.

STAGE 2: 2-Iodo-6-methoxypyrazine was prepared from 2,6-di-iodopyrazine by the method of Example 15, Stage 2.

STAGE 3: 2,2-Dimethyl-3-(6-methoxypyraz-2-yl)-octan-3-ol was prepared from 2-iodo-6-methoxypyrazine by the method of Example 5.

The following Examples 17 and 18 illustrate the plant growth regulator properties exhibited by the compounds of the present invention.

EXAMPLE 17

Results are presented for compounds 1–10, 12–18, 26, 27 and 29, of Table 1, which were tested for plant growth regulator activity against three species for various growth effects relevant to plant growth regulation.

Methodoloqy

The plant species used in this screen are presented in Table VIII with the leaf stage at which they were sprayed. Each chemical was applied at either 4000 ppm or 2000 ppm (4 kg ha$^{-1}$ or 2 kg ha$^{-1}$ in a 1000 l ha$^{-1}$ field volume) using a tracksprayer and a SS8004E (Teejet) nozzle.

After spray the plants were grown in a glasshouse with 25° C. day/22° C. night temperatures and supplementary lighting was supplied when necessary (from mercury vapour lamps), to provide a 16 hour photoperiod. The exception to this were the temperate cereals, wheat and barley which were grown in 16° C. day/13° C. night temperatures.

After 2–6 weeks in the glasshouse, depending on the time of year, the plants were visually assessed for morphological characteristics. Formulation blanks were used as controls to assess the plants. The results are presented in Tables IX–XI.

TABLE IX

| | | Winter Wheat | | | | |
| --- | --- | --- | --- | --- | --- | --- |
| COMPOUND NO. | RATE (PPM) | R | G | A | T | I |
| 1 | 4000 | 2 | 1 | | 3 | 3 |
| 2 | 2000 | 3 | 1 | | 2 | 3 |
| 3 | 4000 | 2 | | | | 2 |
| 4 | 4000 | 2 | | | | 2 |
| 5 | 4000 | 3 | | | 3 | 3 |
| 6 | 4000 | 3 | 3 | | 3 | 3 |
| 7 | 4000 | 3 | 2 | | 3 | 3 |
| 8 | 4000 | 3 | 3 | | 2 | 3 |
| 9 | 4000 | | | | | |
| 10 | 2000 | 2 | 1 | | | 2 |
| 12 | 4000 | | | | | |
| 13 | 4000 | | | | | |
| 14 | 2000 | 2 | 1 | | | 2 |
| 15 | 4000 | | | | | |
| 16 | 2000 | 3 | 2 | | 2 | 3 |
| 17 | 4000 | 1 | | | 1 | 1 |
| 18 | 2000 | 1 | | | 1 | 1 |
| 26 | 4000 | | | | | |
| 27 | 4000 | 2 | | | | 2 |
| 29 | 4000 | 1 | | | | 1 |

TABLE VIII

Plant Material used for Whole Plant Screen

| Species | Code | Variety | Growth Stage at Treatment | No Plants per 3" Pot | Compost Type |
| --- | --- | --- | --- | --- | --- |
| Barley | BR | Atem | 1–1.5 leaves | 4 | JIP* |
| Wheat | WW | Timmo | 1–1.5 leaves | 4 | JIP |
| Tomato | To | Ailsa Craig | 2½ leaves | 1 | PEAT |

JIP* = John Innes Potting Compost.

TABLE X

| COMPOUND NO. | RATE Kg ha$^{-1}$ | R | G | A | T | I |
|---|---|---|---|---|---|---|
| 1 | 4000 | 3 | 1 | | 2 | 3 |
| 2 | 2000 | 2 | 1 | | 1 | 2 |
| 3 | 4000 | 2 | | | 1 | 3 |
| 4 | 4000 | 2 | | | 1 | 3 |
| 5 | 4000 | 2 | | | 2 | 3 |
| 6 | 4000 | 2 | 1 | | 2 | 3 |
| 7 | 4000 | 2 | 1 | | 2 | 2 |
| 8 | 4000 | 2 | 1 | | 1 | 3 |
| 9 | 4000 | | | | 1 | |
| 10 | 2000 | 1 | | | 1 | 1 |
| 12 | 4000 | 1 | | | 3 | 1 |
| 13 | 4000 | 2 | 1 | | | 2 |
| 14 | 2000 | | | | | |
| 15 | 4000 | | | | | |
| 16 | 2000 | 2 | | | | 2 |
| 17 | 4000 | | | | | |
| 18 | 2000 | 2 | | | | 2 |
| 26 | 4000 | | | | | |
| 27 | 4000 | | | | | |
| 29 | 4000 | | | | | |

Barley

TABLE XI

Tomato

| COMPOUND NO. | RATE Kg ha$^{-1}$ | R | G | A | T | I |
|---|---|---|---|---|---|---|
| 1 | 4000 | 2 | 2 | | | 2 |
| 2 | 2000 | | | | | |
| 3 | 4000 | 3 | | | | 3 |
| 4 | 4000 | 3 | | | | 3 |
| 5 | 4000 | 1 | | | | 2 |
| 6 | 4000 | 1 | | | | 1 |
| 7 | 4000 | 2 | | | | 2 |
| 8 | 4000 | 2 | 2 | | | 2 |
| 9 | 4000 | | | | 1 | |
| 10 | 2000 | | | | | |
| 12 | 4000 | 2 | | | | 1 |
| 13 | 4000 | | | | | |
| 14 | 2000 | | | | | |
| 15 | 4000 | | | | | |
| 16 | 2000 | 1 | 1 | | | 1 |
| 17 | 4000 | 1 | | | | 2 |
| 18 | 2000 | 2 | 1 | | | 2 |
| 26 | 4000 | 2 | 1 | | | 2 |
| 27 | 4000 | | | | | |
| 29 | 4000 | | | | | |

Key:
R = Retardation
G = Greening effect
A = Apical damage
T = Tillering or side shooting
I = Interligular or internodal length reduction
All effects are scored visually on a 1-3 basis where
1 = 10-30%
2 = 31-60%
3 = 61-100%
Blank means less than 10% effect.

EXAMPLE 18

Intermediate Retardant Test

Methodology

Three species are involved in this test RICE, SPRING-BARLEY and APPLES. The variety and growth stages at spray are outlined in Table XII. Compounds were applied at 500 ppm and 2000 ppm respectively (0.5 kg and 2 kg ha$^{-1}$ at a field volume of 1000 l ha$^{-1}$) as an overall spray. This gives a foliar and root component in the test, i.e., this test will detect the activity of both root and foliar acting compounds. The exception was a root drench application on apples at a rate of 2 kg ha$^{-1}$ in addition to a 2 kg ha$^{-1}$ foliar only spray. The rice was grown in 4" 'paddy' pots, i.e., the roots and bottom of the stems are immersed in water under conditions corresponding to those in paddy fields. Spring barley and apples were grown in 4" pots. The plants were assessed for height to top-most ligule at approximately 28 days after treatment for spring barley and rice and for height to apex at approximately 28 days after the treatment for apples. In each case the result for each compound is compared to the height of the formulation blank in that test and presented as a percentage reduction in height compared to the formulation blank. A blank indicates that the compound was substantially inactive as a retardant at that particular rate of application.

Compound No. 16 of Table 1 was applied to rice, barley and apples as outlined above and also to oilseed rape (*Brassica napus*) as a foliar spray and as a root drench, all at 1000 ppm (1 kg ha$^{-1}$). Assessments were made at 21 days after treatment. The results are presented in Tables XIII–XVI.

TABLE XII

Plant Material for Intermediate Retardant Test

| SPECIES | VARIETY | GROWTH STAGE AT TREATMENT | NO. PLANTS PER 4" POT | Compost |
|---|---|---|---|---|
| Spring Barley | Atem | 3 leaves | 4 | JIP 1 |
| Rice | Ishikari | 3-4 leaves | 2 | GRIT:JIP 3 |
| Apples | Red Delicious | 5-10 cm high | 1 | GRIT:JIP 3 |
| Oilseed Rape (*Brassica napus*) | | 3-4 leaves | 1 | JIP 1 |

JIP 1 = John Innes Potting Compost.

TABLE XIII

Rice - % Reduction

| COMPOUND NO. | 500 g/ha | 2000 g/ha |
|---|---|---|
| 1 | 35 | 56 |
| 2 | 9 | 28 |
| 27 | 3 | 7 |
| 3 | 1 | 15 |
| 4 | 13 | 8 |
| 5 | 0 | 0 |
| 6 | 7 | 0 |
| 7 | 0 | 0 |
| 8 | 0 | 0 |
| 29 | 0 | 0 |
| 17 | 0 | 0 |
| 26 | 0 | 0 |
| 16 | — | 25 (1000 g/ha) |

TABLE XIV

Spring Barley - % Reduction

| COMPOUND NO. | 500 g/ha | 2000 g/ha |
|---|---|---|
| 1 | 58 | 79 |
| 2 | 40 | 66 |

TABLE XIV-continued

| | Spring Barley - % Reduction | |
|---|---|---|
| COMPOUND NO. | 500 g/ha | 2000 g/ha |
| 27 | 8 | 6 |
| 3 | 11 | 34 |
| 4 | 11 | 14 |
| 5 | 0 | 8 |
| 6 | 11 | 11 |
| 7 | 9 | 9 |
| 8 | 12 | 16 |
| 29 | 0 | 3 |
| 17 | 0 | |
| 26 | 7 | 16 |
| 16 | — | 48 |
| | | (1000 g/ha) |

TABLE XV

| | Apples - % Reduction | |
|---|---|---|
| COMPOUND NO. | Foliar Only 2000 g/ha | Root Drench 2000 g/ha |
| 1 | 0 | 0 |
| 2 | 0 | 16 |
| 27 | 0 | 17 |
| 3 | 0 | 0 |
| 4 | 2 | 3 |
| 5 | 0 | 0 |
| 6 | 0 | 0 |
| 7 | 0 | 0 |
| 8 | 0 | 14 |
| 29 | 0 | 2 |
| 17 | 5 | 0 |
| 26 | 15 | 24 |
| 16 | — | 17 |
| | | (1000 g/ha) |

TABLE XVI

| | Oilseed Rape - % Reduction | |
|---|---|---|
| COMPOUND NO. | FOLIAR ONLY 1000 g/ha | ROOT DRENCH 1000 g/ha |
| 16 | 20 | 9 |

The manner in which the compounds of the present invention may be formulated into compositions suitable for application is shown generally in the following indicative illustrations numbered as Examples 19 to 28.

EXAMPLE 19

An emulsifiable concentrate is made up by mixing the following ingredients, and stirring the mixture until all the constituents were dissolved.

| | |
|---|---|
| Compound of Table I | 10% |
| Calcium dodecylbenzensulphate | 5% |
| "SYNPERONIC" NP13 | 5% |
| "Aromasol" H | 80% |

EXAMPLE 20

A composition in the form of grains readily dispersible in a liquid, e.g. water, is prepared by grinding together the first three ingredients in the presence of added water and then mixing in the sodium acetate. The resultant mixture is dried and passed through a British Standard mesh sieve, size 44–100, to obtain the desired size of grains.

| | |
|---|---|
| Compound of Table I | 50% |
| "Dispersol" T | 25% |
| "SYNPERONIC" NP5 | 1.5% |
| Sodium acetate | 23.5% |

EXAMPLE 21

The following ingredients are ground together to produce a powder formulation readily dispersible in liquids.

| | |
|---|---|
| Compound of Table I | 45% |
| "Dispersol" T | 5% |
| "SYNPERONIC" NX | 0.5% |
| "Cellofas" B600 | 2% |
| China clay GTY powder | 47.5% |

EXAMPLE 22

The active ingredient is dissolved in acetone and the resultant liquid is sprayed on to the granules of attapulgite clay. The solvent is then allowed to evaporate to produce a granular composition.

| | |
|---|---|
| Compound of Table I | 5% |
| Attapulgite granules | 95% |

EXAMPLE 23

A composition suitable for use as a seed dressing is prepared by mixing the three ingredients.

| | |
|---|---|
| Compound of Table I | 50% |
| Mineral oil | 2% |
| China clay | 48% |

EXAMPLE 24

A dusting powder is prepared by mixing the active ingredient with talc.

| | |
|---|---|
| Compound of Table I | 5% |
| Talc | 95% |

EXAMPLE 25

A flowable formulation is prepared by bead-milling the constituents set out below and then forming an aqueous suspension of the ground mixture with water.

| | |
|---|---|
| Compound of Table I | 40% |
| "Dispersol" T | 4% |
| "SYNPERONIC" NP5 | 1% |
| Water | 55% |

EXAMPLE 26

A dispersible powder formulation is made by mixing together the ingredients set out below and then grinding the mixture until all were thoroughly mixed.

| | |
|---|---|
| Compound of Table I | 25% |
| "Aerosol" OT/B | 2% |
| "Dispersol" A.C. | 5% |
| China clay | 28% |

| -continued | |
|---|---|
| Silica | 40% |

EXAMPLE 27

This example illustrates the preparation of a dispersible powder formulation. The ingredients are mixed and the mixture then gound in a comminution mill.

| Compound of Table I | 25% |
|---|---|
| "PERMINAL" BX | 1% |
| "Dispersol" T | 5% |
| Polyvinylpyrrolidone | 10% |
| Silica | 25% |
| China clay | 34% |

EXAMPLE 28

The ingredients set out below are formulated into dispersible powder by mixing then grinding the ingredients.

| Compound of Table I | 25% |
|---|---|
| "Aerosol" OT/B | 2% |
| "Dispersol" A | 5% |
| China clay | 68% |

In Examples 19 to 28 the proportions of the ingredients given are by weight.

There now follows an explanation of the compositions or substances represented by the various Trade Marks and Trade Names mentioned above.

"SYNPERONIC" NP13 : a condensate of nonyl phenol (1 mole) with ethylene oxide (13 moles).

"AROMASOL" H : a solvent mixture of alkylbenzenes.

"DISPERSOL" T AND AC : a mixture of sodium sulphate and a condensate of formaldehyde with sodium naphthalene sulphonate.

"SYNPERONIC" NP5: a condensate of nonyl phenol (1 mole) with naphthalene oxide (5.5 moles).

CELLOFAS B600 : a sodium carboxymethyl cellulose thickener.

We claim:

1. A pyrazine compound having the formula (I):

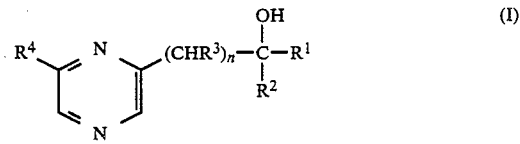

and stereoisomers thereof, wherein $R^1$ is $C_1$-$C_4$ alkyl optionally substituted with halogen, or cyclopropyl optionally substituted with $C_1$-$C_4$ alkyl; $R^2$ is phenylalkynyl optionally substituted on the ring group with one or more halogens; $R^3$ is hydrogen or $C_1$-$C_4$ alkyl; $R^4$ is hydrogen, $C_1$-$C_4$ alkyl, halogen, alkylamino, cyano, or alkoxy; n is 0 or 1 and plant growth regulating salts, acetates or benzoates thereof.

2. A derivative according to claim 1 wherein $R^1$ is isopropyl, cyclopropyl, 1-methylcyclopropyl or tertiary butyl.

3. A derivative according to claim 1 wherein $R^4$ is hydrogen and n is 0.

4. A derivative according to claim 1 wherein $R^2$ is the group, $$-C\equiv C-R^6$$

where $R^6$ is a phenyl group optionally substituted with halogen.

5. A plant growth regulating composition comprising a plant growth regulating amount of a pyrazine derivative according to claim 1 and an agrochemically acceptable carrier or diluent.

6. A method of regulating plant growth which comprises applying to the plant, to the seed of the plant, or to the locus of the plant or seed a plant growth regulating amount of a pyrazine derivative according to claim 1 and an agrochemically acceptable carrier or diluent.

* * * * *